US009554839B2

(12) United States Patent
Lin et al.

(10) Patent No.: US 9,554,839 B2
(45) Date of Patent: Jan. 31, 2017

(54) INJECTION DEVICE AND HEATING UNIT THEREOF

(71) Applicant: INDUSTRIAL TECHNOLOGY RESEARCH INSTITUTE, Hsin-Chu (TW)

(72) Inventors: Ying-Tso Lin, Hsinchu County (TW); Chi-Feng Chan, Chiayi County (TW); Chieh Hu, Chiayi (TW); Chun-Jen Liao, Taipei (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 846 days.

(21) Appl. No.: 13/945,413

(22) Filed: Jul. 18, 2013

(65) Prior Publication Data
US 2014/0163567 A1 Jun. 12, 2014

(30) Foreign Application Priority Data

Dec. 7, 2012 (TW) .............................. 101146093 A

(51) Int. Cl.
*A61B 17/88* (2006.01)
*H05B 3/00* (2006.01)
*H05B 3/42* (2006.01)

(52) U.S. Cl.
CPC ............. *A61B 17/8836* (2013.01); *H05B 3/42* (2013.01); *A61B 17/8822* (2013.01)

(58) Field of Classification Search
CPC ....... H05B 3/42; B29C 45/74; A61B 17/8836; A61B 17/8822
See application file for complete search history.

(56) References Cited

U.S. PATENT DOCUMENTS

| 3,588,956 A * | 6/1971 | Poux ....................... B29C 45/74 |
| | | 425/192 R |
| 4,183,448 A * | 1/1980 | Nash ....................... B29C 45/50 |
| | | 222/146.5 |
| 4,711,250 A | 12/1987 | Gilbaugh, Jr. et al. |
| 4,807,597 A * | 2/1989 | Tsuno ................ A61B 1/00165 |
| | | 600/129 |
| 4,992,045 A | 2/1991 | Beisel |
| 5,064,426 A | 11/1991 | Huebsch |
| 5,614,227 A * | 3/1997 | Yarbrough ................ B29B 7/46 |
| | | 366/83 |

(Continued)

OTHER PUBLICATIONS

Intellectual Property Office, Ministry of Economic Affairs, R.O.C., "Office Action", May 19, 2015, Taiwan.

(Continued)

*Primary Examiner* — Yogendra Gupta
*Assistant Examiner* — Emmanuel S Luk
(74) *Attorney, Agent, or Firm* — Locke Lord LLP; Tim Tingkang Xia, Esq.

(57) ABSTRACT

An injection device includes a housing, a plunger, and a heating unit. The plunger is slidably arranged within the housing thereby performing a plunging movement therein. The heating unit is disposed within the housing for generating a heat energy inside the housing such that a filling material inside the housing can be soften and be transformed into a movable filling material with viscosity by absorbing the heat energy from the heating unit.

13 Claims, 7 Drawing Sheets

(56) References Cited

U.S. PATENT DOCUMENTS

| | | | | |
|---|---|---|---|---|
| 6,121,341 | A * | 9/2000 | Sawhney | A61L 24/0015 128/898 |
| 6,436,143 | B1 | 8/2002 | Ross et al. | |
| 6,517,534 | B1 * | 2/2003 | McGovern | A61B 18/1485 606/28 |
| 7,244,393 | B2 * | 7/2007 | Kaylor | B01L 3/5023 422/412 |
| 7,264,757 | B2 * | 9/2007 | Chang | B29C 44/3446 264/50 |
| 7,559,932 | B2 * | 7/2009 | Truckai | A61B 17/8836 606/92 |
| 7,722,620 | B2 * | 5/2010 | Truckai | A61B 17/8822 606/93 |
| 7,771,426 | B2 | 8/2010 | Burch et al. | |
| 8,007,709 | B2 * | 8/2011 | Taylor | B29C 47/827 264/472 |
| 8,109,933 | B2 | 2/2012 | Truckai et al. | |
| 8,128,626 | B2 | 3/2012 | Justin | |
| 8,430,887 | B2 * | 4/2013 | Truckai | A61B 17/8816 606/94 |
| 8,487,021 | B2 * | 7/2013 | Truckai | A61L 24/0089 523/116 |
| 8,591,218 | B2 * | 11/2013 | Kawasaki | B29C 45/74 264/328.14 |
| 2006/0122622 | A1 | 6/2006 | Truckai et al. | |
| 2007/0127870 | A1 | 6/2007 | Oron et al. | |
| 2007/0233148 | A1 | 10/2007 | Truckai et al. | |
| 2008/0154273 | A1 | 6/2008 | Shadduck et al. | |
| 2008/0269761 | A1 | 10/2008 | Truckai et al. | |
| 2009/0306674 | A1 | 12/2009 | Chandler | |
| 2011/0137318 | A1 | 6/2011 | Liao et al. | |
| 2011/0144614 | A1 * | 6/2011 | Hereford | A61J 1/2096 604/414 |
| 2014/0027095 | A1 * | 1/2014 | Warchol | B23P 15/00 165/87 |

OTHER PUBLICATIONS

Mark J. Mondrinos et al., Porogen-based solid freeform fabrication of polycaprolactone-calcium phosphate scaffolds for tissue engineering, Biomaterials, 2006, p. 4399-4408, vol. 27.

Imad Al-Assir et al., Percutaneous Vertebroplasty: A Special Syringe for Cement Injection, AJNR Am J. Neuroradiol, 2000, p. 159-161, vol. 21.

Xiaopeng Qi et al., Improved injectability and in vitro degradation of a calcium phosphate cement containing poly (lactide-co-glycolide) microspheres, Elsevier, Acta Biomaterialia, 2008, p. 1837-1845, vol. 4.

Lotfi Hacein-Bey, Current and emerging treatment strategies for vertebral compression fractures, Orthopedic Research and Reviews, 2012, p. 65-75, vol. 4.

C. V. Rahman et al., Chemistry of Polymer and Ceramic-Based Injectable Scaffolds and Their Applications in Regenerative Medicine, Chemistry of Materials, 2012, p. 781-795, vol. 24.

* cited by examiner

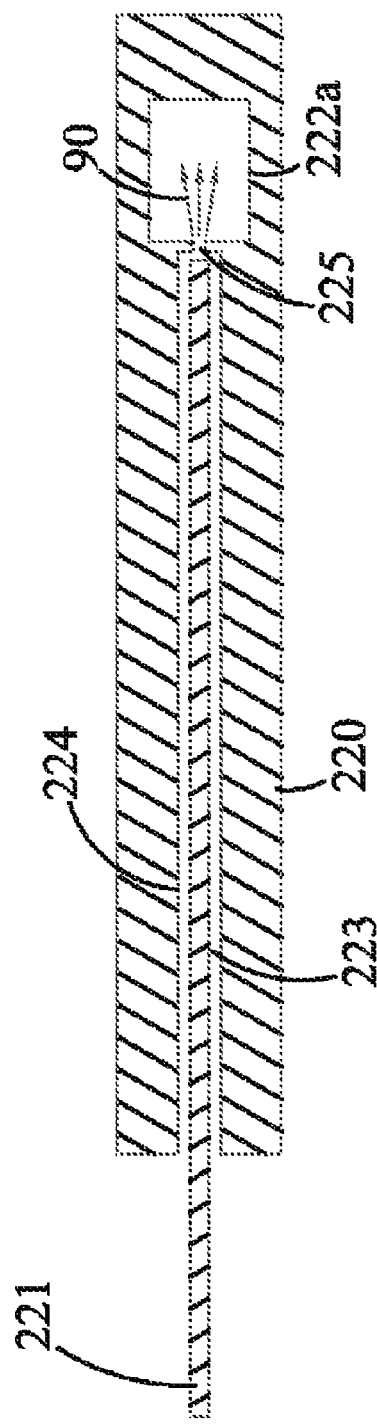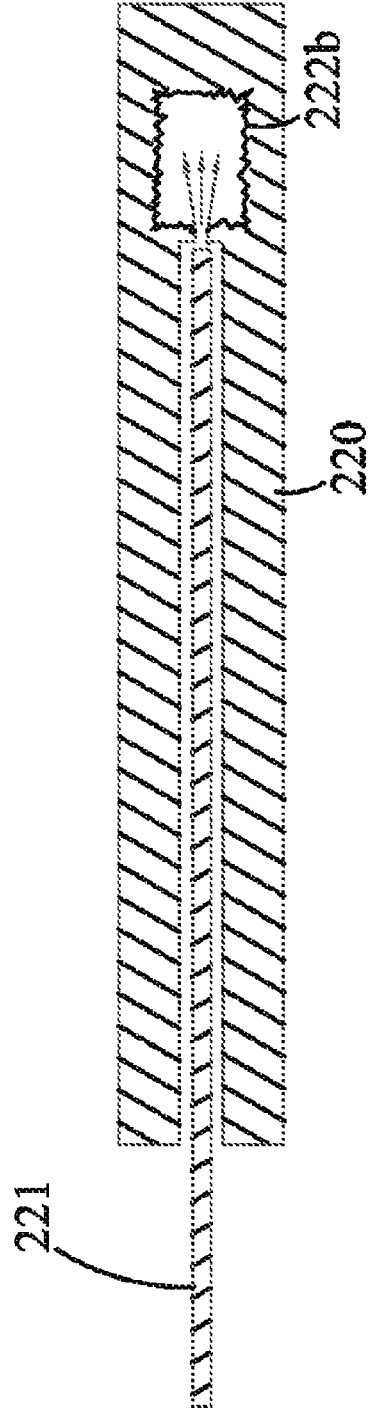
FIG.3A
FIG.3B

INJECTION DEVICE AND HEATING UNIT THEREOF

CROSS REFERENCE TO RELATED APPLICATION

This application also claims priority to Taiwan Patent Application No. 101146093 filed in the Taiwan Patent Office on Dec. 7, 2012, the entire content of which is incorporated herein by reference.

TECHNICAL FIELD

The technical field relates to an injection device and heating unit.

BACKGROUND

According to a research performed by the National Osteoporosis Foundation of USA, spinal compression fracture is the most common complication induced by osteoporosis. At Year 2009, there are about forty-four million people suffered from osteoporosis in U.S.A., and that amount will increase dramatically to sixty-one million at Year 2020. Moreover, there are about one and a half million bone fracture instances that are directly caused by osteoporosis in U.S.A only at Year 2009, and among which seven hundred thousands of that are compression fracture. There are similar conditions happening in Taiwan. In a recent research focused upon the population over the age of 65, there are about five hundred thousands people suffered from osteoporosis which makes the osteoporosis the cause of the second popular chronic disease in Taiwan, and in addition, there are nearly sixty thousands cases of compression fracture are caused directly from osteoporosis.

The common methods for treating osteoporosis include nerve decompression surgery and vertebral fusion surgery of heterogous/autologous bone transplantation. However, such common surgical methods are disadvantageous in that: longer operation time, larger wound incision and longer healing period. Among those common surgical methods, the procedure of autologous bone transplantation is most effective, but it requires one additional wound incision for harvesting a health bone from the patient. On the other hand, for the heterogous bone transplantation, the problems of complication, such as bone graft resorption and infection, can be serious.

In recent years, with the rapid improvement in micro-invasive surgical technique and instrument, there are more and more micro-invasive surgical procedures being developed for treating painful spinal compression fractures, whereas one of the exemplary micro-invasive surgical procedures is the vertebroplasty procedure. Since the pain induced from a spinal compression fracture is generally resulting from the instability and motion of fractured vertebrae, such pain can be relieved when the fractured vertebrae is stabilized by filling the cracks in the fractured vertebrae and enhancing the vertebral strength. In a vertebroplasty the filling of bone cement is performed under the assistance of X-ray imaging, and after the bone cement is cured, the fractured vertebrae can be fixed motionlessly and correctly so that the stability and compression resistance of vertebral body are increased. Moreover, since the vertebroplasty procedure is considered a minimally invasive surgical procedure that can be done through a small puncture in the patient's skin as opposed to an open incision and with less recovery time, most patients receiving the procedure generally experience significant pain relief of more than 80% that allows the patients to return to their normal activity shortly after the procedure.

SUMMARY

The one of embodiments relates to an injection device which has a heat source embedded therein while allowing the temperature of the injection device to descent according to a temperature gradient from the center of the heat source to the surface of the injection device, and thereby, reducing the exterior temperature of the injection device. Moreover, by the internal heat source of the injection device, a filling material inside the injection device can be soften and transformed into a movable filling material with viscosity so as to be injected into a target object.

The one of embodiments relates to an injection device, which is devised to guide an electromagnetic wave (e.g. a laser beam) through fiber optical fibers to a plastic material for heating and softening the same, and thereafter, to injected the softened plastic material into a target object to be cured.

The one of embodiments relates to an injection device, which has an electric heater embedded therein to be used for heating and softening a plastic material filled inside the injection device, and thereafter, to injected the softened plastic material into a target object to be cured.

The one of embodiments relates to an injection device, which is devised to guide an electromagnetic wave using a light-guide element disposed inside a heating chamber of the injection device to a light absorbing element, by that the energy of the electromagnetic wave is absorbed by the light absorbing element, and thus, the temperature of the light absorbing element is raised so as to emit and transmit heat to the heating chamber.

In an exemplary embodiment, the present disclosure provides an injection device, which comprises: a housing; a plunger, slidably arranged within the housing for enabling the same to perform a plunging movement therein; and a heating unit, disposed within the housing while allowing a passage to be formed between the heating unit and an inner wall of the housing.

In another exemplary embodiment, the present disclosure provides an heating unit, which comprises: a heating chamber, having a space formed therein by the enclosure of an inner wall thereof; a light-guide element, disposed inside the space for guiding the travelling of an electromagnetic wave; and a light absorbing element, coupled to the light-guide element for allowing the same to receive the electromagnetic wave so as to generate a heat energy to be transmitted to the heating chamber.

In further another exemplary embodiment, the present disclosure provides an injection device, devised to heat and then inject a biomedical material, such as a bone cement.

BRIEF DESCRIPTION OF THE DRAWINGS

The present disclosure will become more fully understood from the detailed description given herein below and the accompanying drawings which are given by way of illustration only, and thus are not limitative of the present disclosure and wherein:

FIG. 3A and FIG. 3B are schematic diagrams showing various exemplary light absorbing elements used in the present disclosure.

DETAILED DESCRIPTION

Figure 1A:
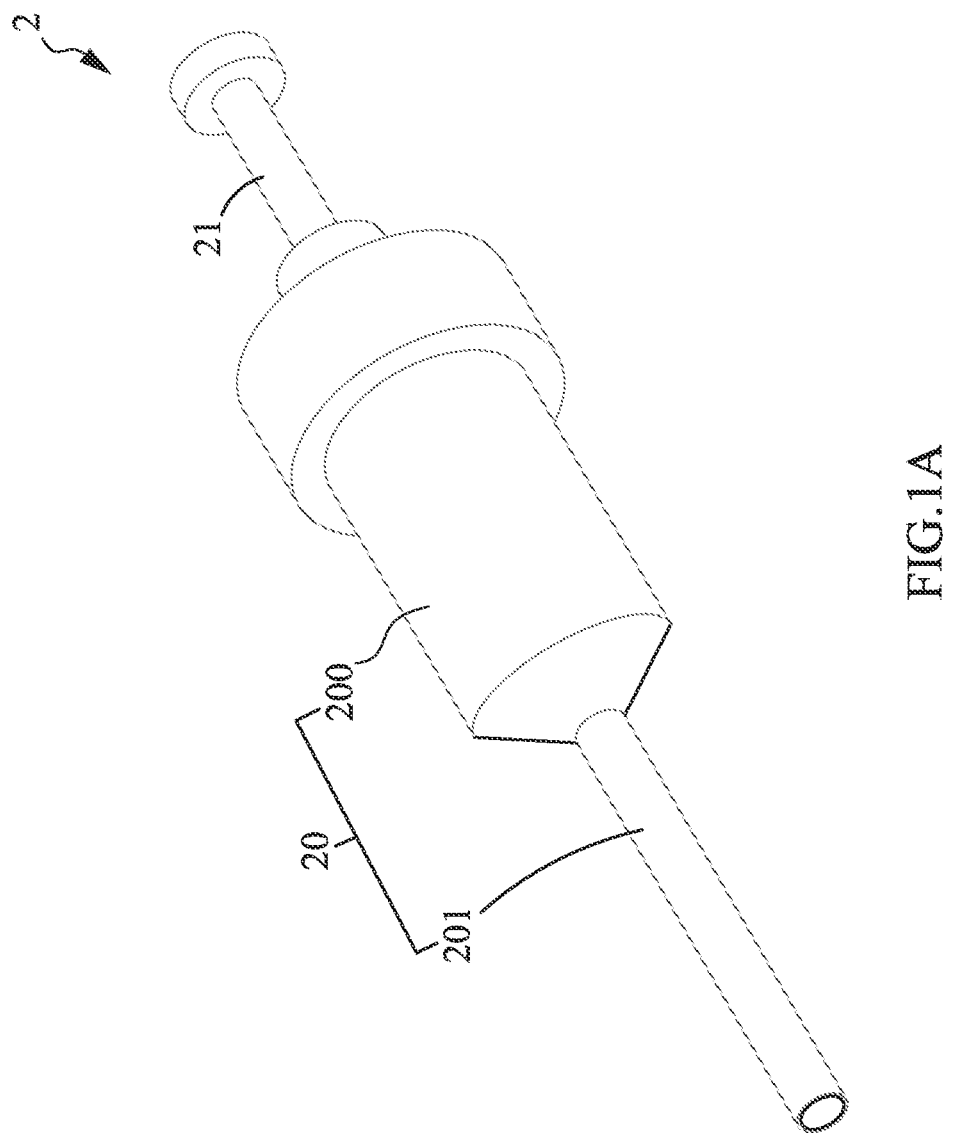
FIG. 1A and FIG. 1B are respectively a three-dimensional view and a partial cross-sectional view of an injection device according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1B:
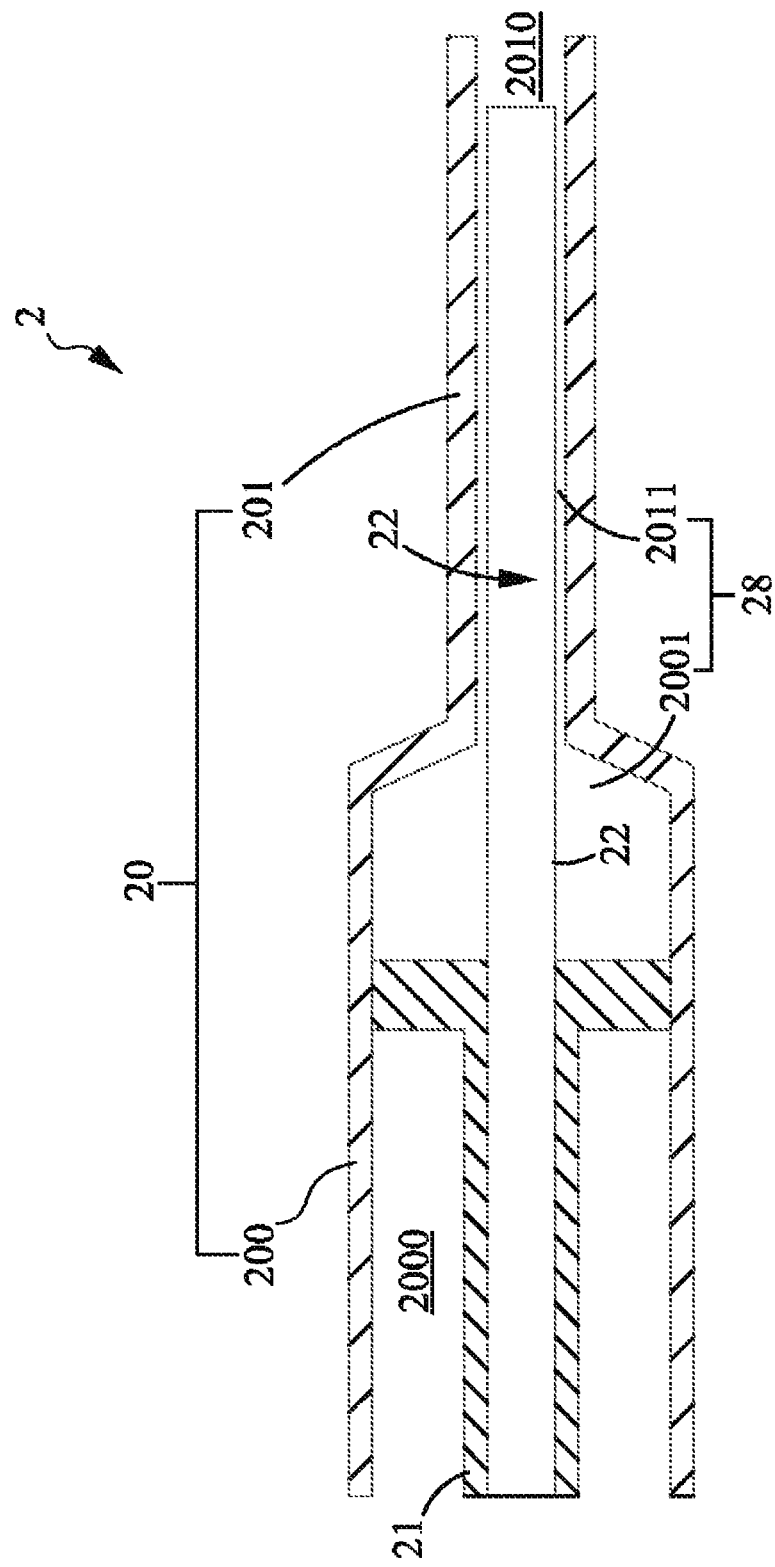

Please refer to FIG. 1A and FIG. 1B, which are respectively a three-dimensional view and a partial cross-sectional view of an injection device according to an embodiment of the present disclosure. In the exemplary embodiment shown in FIG. 1A and FIG. 1B, the injection device 2 comprises: a housing 20, a plunger 21 and a heating unit 22. In addition, the housing 20 is composed of a material supply section 200 and an injection section 201, whereas the material supply section 200 is formed with a first space 2000 and the injection section 201 is formed with a second space 2010, while allowing the first space 2000 to be in fluid communication with the second space 2010. Moreover, the first space 2000 is formed in a caliber larger than that of the second space 2010.

In this embodiment, the plunger 21 is slidably mounted to the inner wall of the housing 20 while being fitted into the first space 2000 of the material supply section 200 for enabling the plunger 21 to perform a plunging movement therein. Moreover, the plunger 21 in this embodiment can substantially be a piston unit, which is capable of performing a reciprocating displacement movement, and such reciprocating displacement movement can be powered either by a electric power supply or by man power whichever is known to those skilled in the art and will not be described further herein. The heating unit 22 is disposed within the housing 20 while allowing a passage 28 to be formed between the heating unit 22 and the inner wall of the housing 20. In this embodiment, the passage 28 is composed of a first channel 2001 and a second channel 2011, and the heating unit 22 is arranged boring through the plunger 21 and extending into the first space 2000 and the second space 2010 of the housing 20, while simultaneously enabling the first channel 2001 to be formed between the outer wall of the heating unit 22 and the portion of the inner wall of the housing 20 that is positioned corresponding to the first space 2000, and also enabling the second channel 2011 to be formed between the outer wall of the heating unit 22 and the portion of the inner wall of the housing 20 that is positioned corresponding to the second space 2010. Accordingly, a filling material disposed inside the first channel 2001 can be forced to move into the second channel 2011 by the pushing of the plunger 21, and the filling material that is forced to move into the second channel 2011 will be heated and softened so as to be transformed into a movable filling material with viscosity that is going to flow out of the housing 20 through an opening formed thereat to be injected into a target object.

Figure 2:
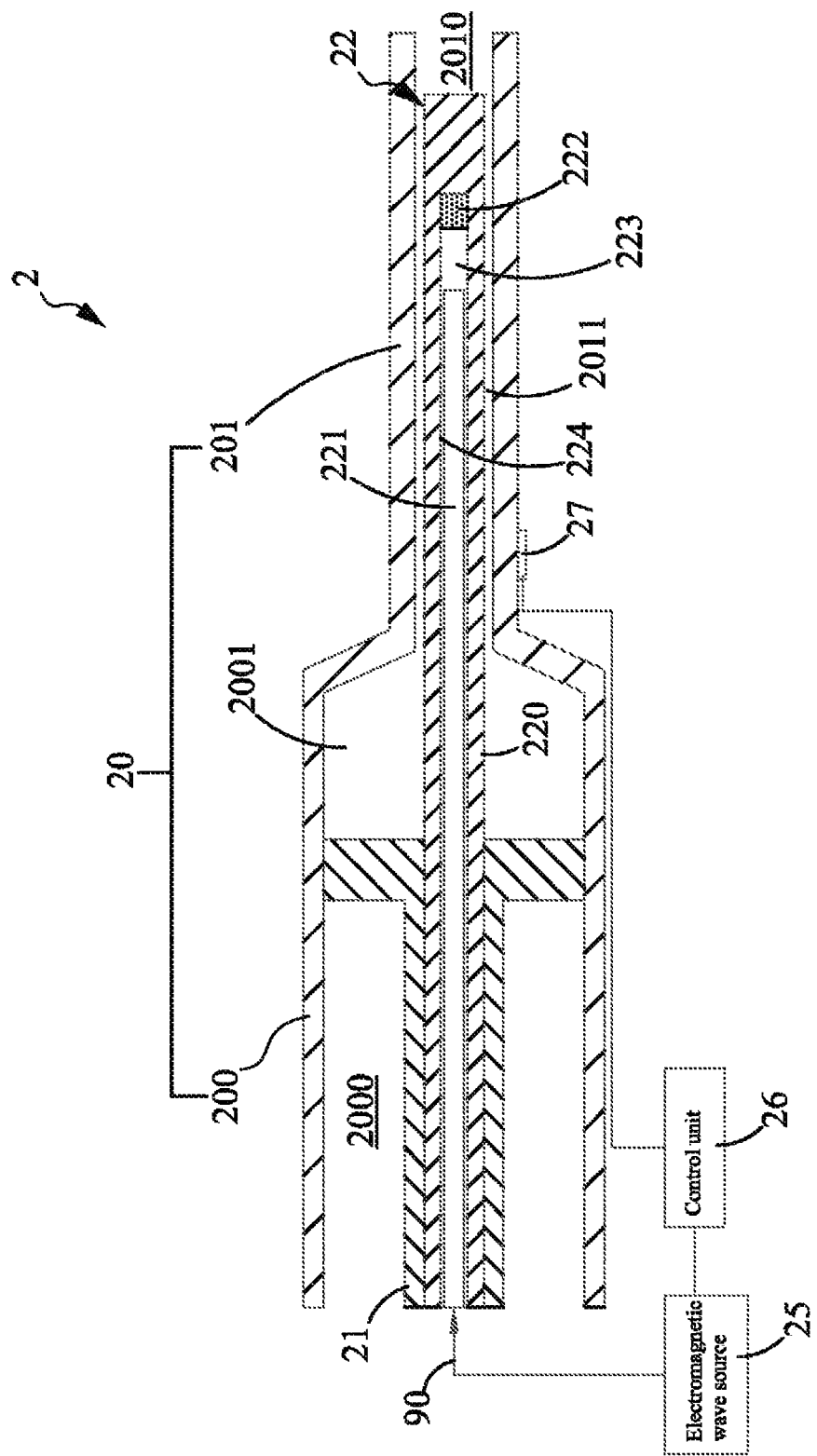
FIG. 2 is a schematic diagram showing a first exemplary heating unit used in the present disclosure.

Please refer to FIG. 2, which is a schematic diagram showing a first exemplary heating unit used in the present disclosure. In this embodiment, the heating unit 22 is composed of: a heating chamber 220, a light-guide element 221 and a light absorbing element, 222. It is noted that this first exemplary heating unit 22 can be an electrical heating unit, and thus the heating chamber 220 can be made of a heat conductive material capable of absorbing electromagnetic waves for generating heat, such as metals. In an embodiment, the heating chamber 220 can be made of a titanium alloy or a stainless steel alloy, but is not limited thereby.

Moreover, there is a cavity 223 formed inside the heating chamber 220 that is formed by the enclosure of the inner wall 224 of the heating chamber 220; and the enclosure of the inner wall 224 has a closed end. In this embodiment, the light-guide element 221 is disposed inside the cavity 223 that can substantially be an optic fiber; and also the light absorbing element 22 is disposed inside the cavity 233 at the closed end of enclosure of the inner wall 224. In an embodiment, the light absorbing element 222 can substantially be a black metal layer that is obtained by a surface treatment process, such as an anodized black treatment. In an embodiment of the present disclosure, the light absorbing element 222 can substantially be a surface-treated metal layer.

In addition, the injection device 2 further includes an electromagnetic wave source 25, a control unit 26 and a temperature sensor 27. The electromagnetic wave source 25 is coupled to the light-guide element 221 for providing an electromagnetic wave 90 to the light-guide element 221. It is noted that the electromagnetic wave is the result of an interaction between an electric field and a magnetic field and is substantially an energy wave propagating in space. In this embodiment, the electromagnetic wave source 25 can be an LED source or a laser source, and the laser source can be a gas laser source, such as a He—Ne laser, or a CO2 laser; or can be a semiconductor laser, such as a GaAs laser, a InGaAsP laser, AlGaInP laser, and so on; or a solid state laser, such as ruby laser or sapphire laser; or a fiber laser, such as a ytterbium doped fiber laser. Moreover, the LED source can be a visible-light emitting LED source or an invisible-light emitting LED source. In addition, the control unit 26 is electrically coupled to the electromagnetic wave source 25 for providing a control signal to the electromagnetic wave source 25 so as to control the generation of the electromagnetic wave; and the temperature sensor 27 is arranged at the housing 20 and electrically coupled to the control unit 26 for sensing the temperature of the housing 20 that is resulting from the light absorbing element 222 after absorbing the electromagnetic wave, and thus generating a sensing signal accordingly to be transmitted to the control unit 26. Thereby, the control unit 26 is enabled to activate or deactivate the electromagnetic wave source 25 according to the sensing signal.

In addition to the heating chamber 220 with closed-end structure and light absorbing element 222 of anodized black treatment that are shown in FIG. 2, there is another exemplary heating chamber and light absorbing element shown in FIG. 3A. In the embodiment shown in FIG. 3A, there is an opening 225 formed on the inner wall 224 of the heating chamber 220 whereas the inner wall 224 is formed with a closed end; and the light absorbing element is formed as a substantially a light absorbing chamber 222a formed inside the heating chamber 220 while being in communication with the cavity 223 through the opening 225. It is noted that the electromagnetic wave that is being transmitted by the light-guide element 221 is able to be transmitted into the light absorbing chamber 222a through the opening 225 for allowing the energy of the electromagnetic wave to be absorbed by the light absorbing chamber 222a. As the electromagnetic wave 90 is transmitted and reflected inside the light absorbing chamber 222a, portions of the electromagnetic wave will be absorbed in each reflection and after a plurality of reflections, the inner wall of the light absorbing chamber 222a can absorb enough energy from the electromagnetic wave 90 and the temperature of the light absorbing chamber will raise accordingly. The table 1 provided hereinafter is a table illustrating the relationship between the number of reflection and the absorption rate for a beam of 1 μm wavelength when the heating chamber 220 is made of a titanium alloy or a stainless steel alloy.

TABLE 1

| material reflection | Metallic | |
|---|---|---|
| | Absorption rate for titanium alloy | Absorption rate for stainless steel alloy |
| 1 | 40% | 35% |
| 2 | 64% | 58% |
| 5 | 92% | 88% |
| 10 | 99% | 99% |

As shown in Table 1, when the heating chamber 220 is made of a titanium alloy, the absorption rate for a beam of 1 μm in wavelength is larger than 40%. Thus, after one reflection, 40% of the light energy will be absorbed by the inner wall surface of the light absorbing chamber 222a, and after being reflected twice, 64% of the light energy will be absorbed, and eventually, almost 99.4% of light energy will be absorbed after being reflected 10 times. Similarly, for the heating chamber 220 made of a stainless steel alloy, there will also be almost 99% of light energy will be absorbed after being reflected 10 times inside the light absorbing chamber 222a by the inner wall surface thereof. It is noted that the size of the opening can be determined according to actual requirement, and is not restricted by any standard. Moreover, although a beam of 1 μm in wavelength is used in Table 1, it is only used for illustration and thus the wavelength of the laser beam is also determined according to actual requirement without any restriction. In addition, in order to increase the absorption rate of the light absorbing chamber 222a, the inner wall surface of the light absorbing chamber 222a can be formed into a rough surface, as shown in FIG. 3B. Therefore, from the above description, it is concluded that the inner wall surface of the light absorbing chamber 222a can be a rough surface or a smooth surface.

Figure 4:
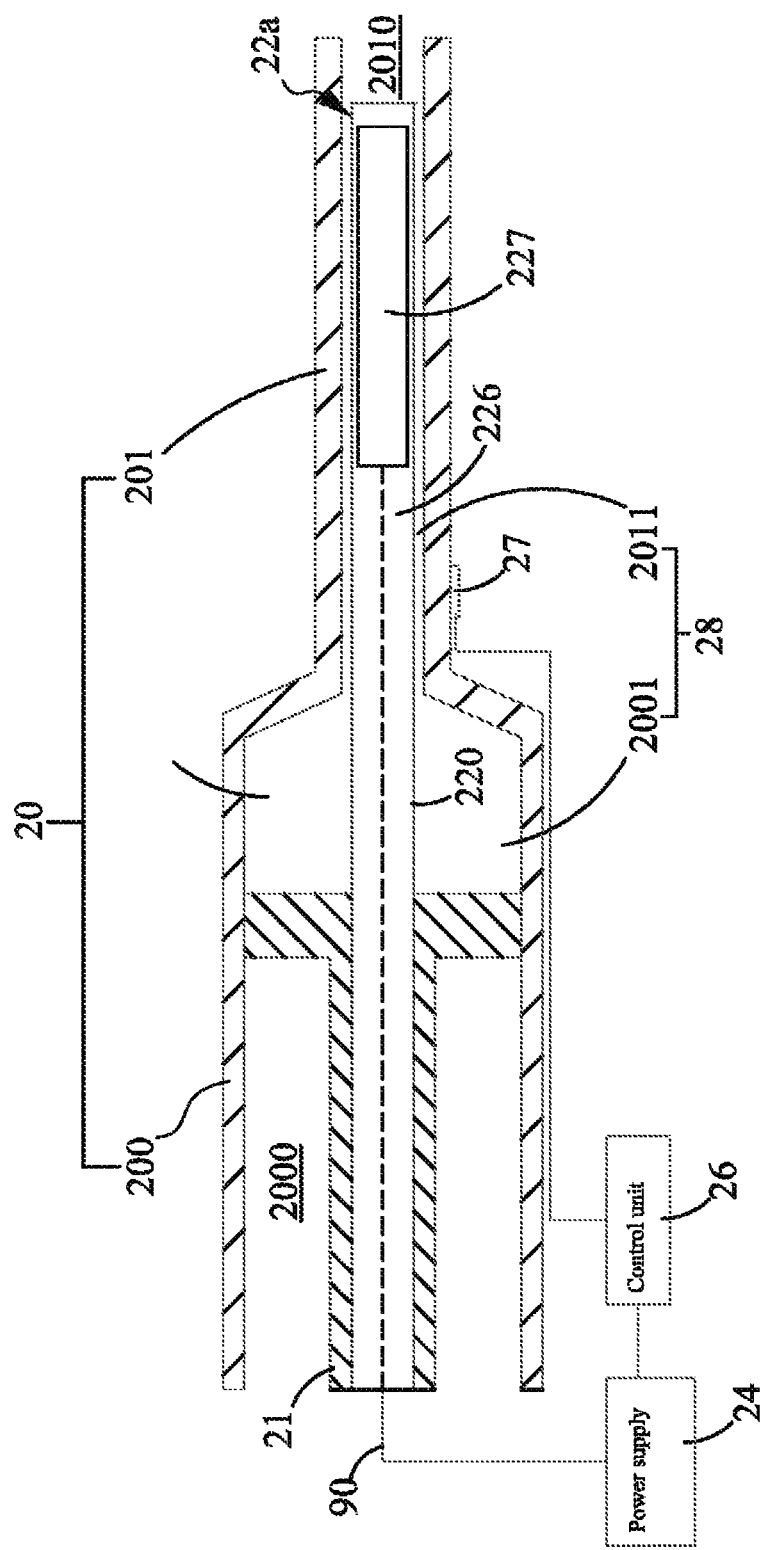
FIG. 4 is a schematic diagram showing a second exemplary heating unit used in the present disclosure.

Please refer to FIG. 4, which is a schematic diagram showing a second exemplary heating unit used in the present disclosure. In this embodiment, the heating unit 22a further includes a frame 226 and a resistance element 227. Moreover, the frame 226 is made of a heat conductive material, such as a metal or alloy. In an embodiment, the frame 226 can be made of a titanium alloy or a stainless steel alloy, but is not limited thereby. As shown in FIG. 4, the frame 226 is arranged boring through the plunger 21 and within the housing 20 so as to enable the passage 28 to be formed between an outer wall of the frame 226 and the inner wall of the housing 20. In this embodiment, the frame 226 is received inside the first space 2000 and the second space 2010 while allowing the first channel 2001 to formed between the outer wall of the frame 226 and the inner wall of the first space 2000 of the housing 20, and the second channel 2011 to be formed between the outer wall of the frame 226 and the inner wall of the second space 2010 of the housing 20. In addition, the resistance element 227 is coupled to the frame 226 for enabling the resistance element 227 to receive and convert an electric energy into a heat energy. In this embodiment, the resistance element 227 is mounted on the frame 226 at a position corresponding to the second space 2010, and in a manner that the resistance element 227 can be embedded inside the frame 226 or attached to the periphery of the frame 226. Moreover, the control unit 26 is further coupled to a power supply 24 for providing the electric energy to the resistance element 227. Similarly, this second exemplary heating unit 22a can be an electrical heating unit, as the one shown in FIG. 2.

Figure 5:
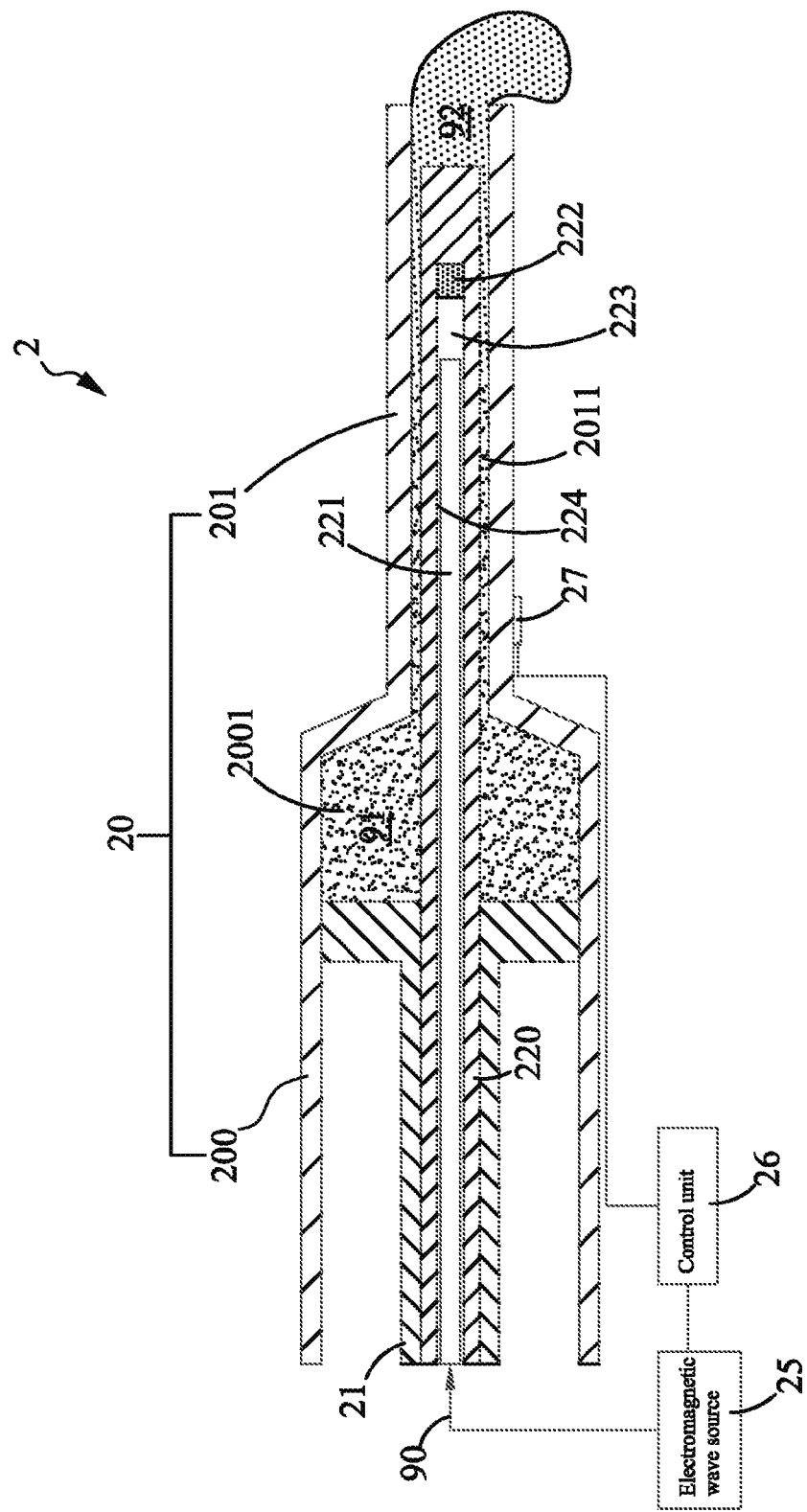
FIG. 5 is a schematic diagram showing the operation of an injection device of the present disclosure.

Please refer to FIG. 5, which is a schematic diagram showing the operation of an injection device of the present disclosure. During the operation of the injection device 2 of FIG. 2, the filling material, such as a bone cement powder 91, is received inside the first channel 2001 that is prepared to be forced to move into the second channel 2011 by the displacement movement of the plunger 21. It is noted that the bone cement powder 91 can be a mixture of PMMA and calcium phosphate cement (CPC), or a mixture of a polymer and CPC, whereas the polymer can be poly(lactic-co-glycolic acid), or polycaprolactone, but is not limited thereby.

At the time when the electromagnetic wave source 25 is activated by the control unit 26 for generating a high-energy electromagnetic wave, the electromagnetic wave will be guided by the light-guide element 221 to be projected onto the light absorbing element 222 where it is to be absorbed. After absorbing the high-energy electromagnetic wave, the temperature of the light absorbing element 22 is raised while allowing the heat to be transmitted to the surface of the heating chamber 220. Meanwhile, the bone cement powder 91 that is forced to move from the first channel 2001 into the second channel 2011 by the plunging movement of the plunger 21 is being positioned at a position corresponding to the light absorbing element 222 and thus enabling the bone cement powder 91 to absorb the heat energy so as to be liquefied into a fluid 92 capable of flowing out of the injection section 201 and injected into a target object. In this embodiment, the target object can be a bone or a vertebra. Moreover, the temperature sensor 27 that is mounted on the housing 20 is used for detecting the temperature of the injection section 201 thereof while feeding back a temperature signal of the detection to the control unit 26 for enabling the control unit 26 to determine whether to activate or deactivate the electromagnetic wave source 25 accordingly. It is noted that when there is run out of bone cement powder 91 is the first channel 2011, it is always capable of enabling the plunger 21 to move reversely out of the housing 20 for refilling the bone cement powder 91 into the housing 20.

The injection device of the present disclosure is featured by its housing 20, especially when the temperature of the injection section 201 is decreased greatly. For instance, in a embodiment when the bone cement powder 91 is heated to a melting temperature of 70° C., the highest temperature that the heating chamber of the present disclosure can achieve is 161° C. Nevertheless, even when the surface temperature of the housing 20 reaches 70° C., the tissue damage caused by the injection device of the present disclosed is greatly reduced since injection device is devised to have a light absorbing element embedded therein for allowing the temperature of the injection device to descent according to a temperature gradient from the center of the light absorbing element to the surface of the injection device, especially the temperature of the injection section 201, and thereby, reducing the exterior temperature of the housing 20 of the injection device. Consequently, the amount of cooling device for cooling the injection device can be decreased, by that the injection section 201 can be made comparatively smaller for micro-invasive surgical procedures. It is noted that the bone cement power used in the aforesaid embodiments is only for illustration, and thus is not limited thereby. Thus, the injection device of the present disclosure can be used for heating, melting and injecting all kinds of filling material in every aspect into any target object at will.

Figure 6:
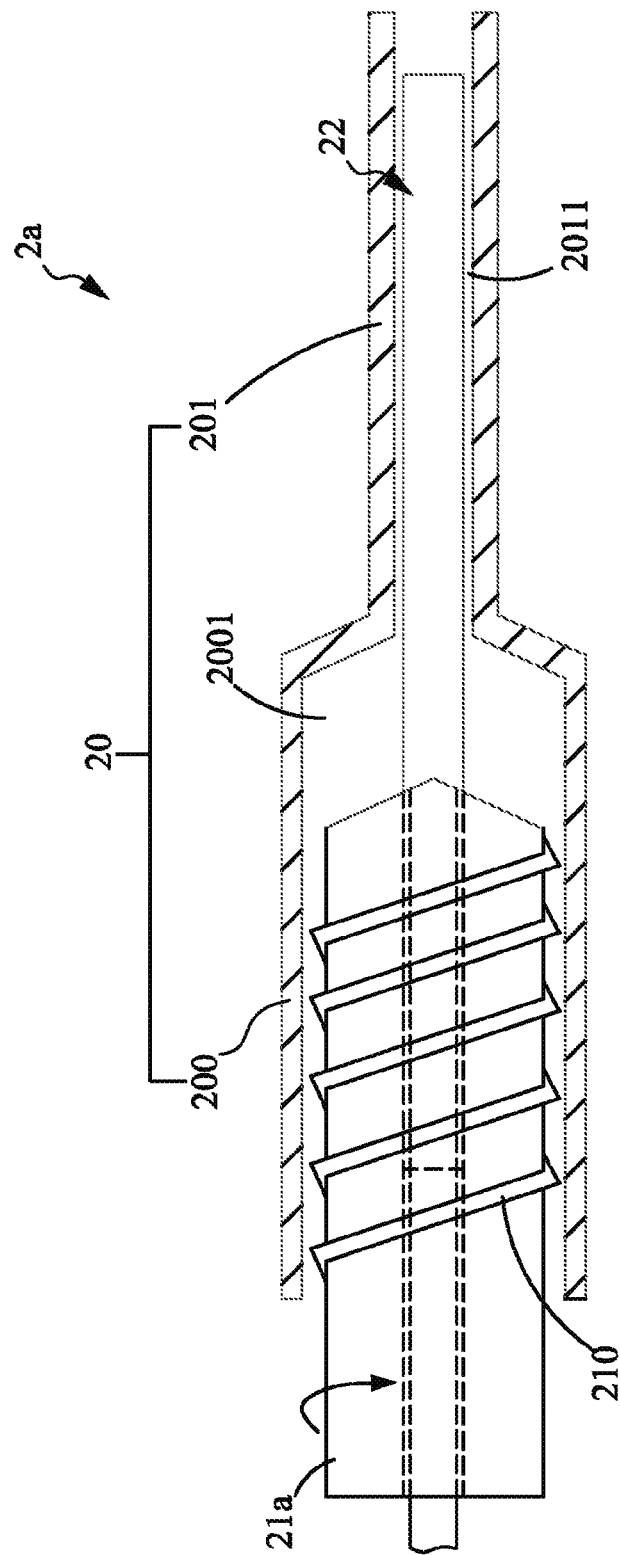
FIG. 6 is a schematic diagram showing an exemplary plunger used in the present disclosure.

Please refer to FIG. 6, which is a schematic diagram showing an exemplary plunger used in the present disclosure. The injection device shown in this embodiment is basically the same as the one shown in FIG. 1B, but is different in that: the plunger 21a in this embodiment is a screw rod unit, and the plunging movement is substantially a rotation movement. As shown in FIG. 6, the screw rod unit 21a has a plurality of threads 210, and thereby the rotating screw rod unit 21a is able to push the bone cement powder in the first channel 2001 to move into the second channel 2011 toward a position corresponding to the light absorbing element for heating and transforming the bone cement powder into a fluid with viscosity. Similarly, such rotation of the screw rod unit 21a can be powered either by a electric power supply or by man power whichever is known to those skilled in the art and will not be described further herein.

Generally, the tissue damage caused by the injection device of the present disclosed is greatly reduced since injection device is devised to have a heat source embedded therein for allowing the exterior temperature of the injection device to descent according to a temperature gradient from the center of the heat source to the surface of the injection device, and consequently, the injection device of the present disclosure can be adapted for biology applications, such as an orthopedic surgery including the filling and injection of bone cement.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. An injection device, which comprises:
  a housing;
  a plunger, slidably arranged within the housing for enabling the same to perform a plunging movement therein; and
  a heating unit, disposed within the housing while allowing a passage to be formed between the heating unit and an inner wall of the housing, and comprising:
    a heating chamber, having a space formed therein by the enclosure of an inner wall thereof while being arranged boring through the plunger and within the housing so as to enable the passage to be formed between an outer wall of the heating chamber and the inner wall of the housing;
    a light-guide element, disposed inside the space for guiding travelling of an electromagnetic wave; and
    a light absorbing element, coupled to the light-guide element for allowing the same to receive the electromagnetic wave so as to generate a heat energy.

2. The injection device of claim 1, wherein the passage is composed of a first channel and a second channel; and the housing is further composed of: a material supply section, arranged at a position corresponding to the first channel for providing a filling material; and an injection section, arranged at a position corresponding to the second channel.

3. The injection device of claim 2, wherein the filling material is forced to move from the first channel into the second channel by the plunging movement of the plunger for positioning the filling material at a position corresponding to the light absorbing element and thus enabling the filling material to absorb the heat energy to be liquefied into a fluid capable of flowing out of the injection section through the first channel.

4. The injection device of claim 1, wherein the light-guide element is substantially an optic fiber.

5. The injection device of claim 1, wherein the light absorbing element is substantially a light absorbing material coated on an end of the inner wall of the heating chamber.

6. The injection device of claim 5, wherein the light absorbing element is substantially a surface-treated metal layer.

7. The injection device of claim 1, wherein the inner wall of the heating chamber is formed with an opening at an end thereof; and the light absorbing element is substantially a light absorbing chamber formed inside the heating chamber while being in communication with the heating chamber through the opening.

8. The injection device of claim 7, wherein an inner wall surface of the light absorbing chamber is formed into a surface selected from the group consisting of: a rough surface and a smooth surface.

9. The injection device of claim 1, further comprising:
  an electromagnetic wave source, coupled to the light-guide element for providing the electromagnetic wave to the light-guide element;
  a control unit, electrically coupled to the electromagnetic wave source for providing a control signal to the electromagnetic wave source so as to control generation of the electromagnetic wave; and
  a temperature sensor, arranged at the housing and electrically coupled to the control unit, for sensing temperature of the housing and thus generating a sensing signal accordingly to be transmitted to the control unit.

10. The injection device of claim 9, wherein the electromagnetic wave source is a source selected from the group consisting of: a laser source and a LED source.

11. The injection device of claim 1, wherein the heating chamber is made of a material selected from the group consisting of: a titanium alloy and a stainless steel alloy.

12. The injection device of claim 1, wherein the plunger is substantially a piston unit, and the plunging movement is substantially a displacement movement.

13. The injection device of claim 1, wherein the plunger is substantially a screw rod unit, and the plunging movement is substantially a rotation movement.

* * * * *